(12) United States Patent
Von Malmborg et al.

(10) Patent No.: US 8,579,832 B2
(45) Date of Patent: Nov. 12, 2013

(54) JOINING OF SENSOR GUIDE WIRE

(75) Inventors: Pär Von Malmborg, Uppsala (SE); Leif Smith, Uppsala (SE)

(73) Assignee: St. Jude Medical Systems AB, Uppsala (SE)

( * ) Notice: Subject to any disclaimer, the term of this patent is extended or adjusted under 35 U.S.C. 154(b) by 671 days.

(21) Appl. No.: 12/739,326

(22) PCT Filed: Oct. 24, 2008

(86) PCT No.: PCT/SE2008/051209
§ 371 (c)(1),
(2), (4) Date: Apr. 22, 2010

(87) PCT Pub. No.: WO2009/054801
PCT Pub. Date: Apr. 30, 2009

(65) Prior Publication Data
US 2010/0222661 A1 Sep. 2, 2010

Related U.S. Application Data

(60) Provisional application No. 60/996,070, filed on Oct. 26, 2007.

(51) Int. Cl.
*A61B 5/00* (2006.01)
*A61B 6/00* (2006.01)
*A61M 25/00* (2006.01)

(52) U.S. Cl.
USPC ........................................ 600/585; 600/434

(58) Field of Classification Search
USPC .......................................................... 600/585
See application file for complete search history.

(56) References Cited

U.S. PATENT DOCUMENTS

| 5,163,445 | A | 11/1992 | Christian et al. |
| 6,529,760 | B2 * | 3/2003 | Pantages et al. ............... 600/407 |
| 6,911,016 | B2 * | 6/2005 | Balzum et al. ............. 604/95.04 |
| 7,758,520 | B2 * | 7/2010 | Griffin et al. .................. 600/585 |
| 8,239,003 | B2 * | 8/2012 | Akins ........................... 600/424 |

FOREIGN PATENT DOCUMENTS

| EP | 1 475 036 B1 | 7/2005 |
| WO | WO 01/54762 A1 | 8/2001 |
| WO | WO 03/084436 A1 | 10/2003 |
| WO | WO 2005/053529 A1 | 6/2005 |

* cited by examiner

*Primary Examiner* — Sean Dougherty
*Assistant Examiner* — Devin Henson
(74) *Attorney, Agent, or Firm* — Foley & Lardner LLP

(57) ABSTRACT

There is a sensor guide wire (1) for intravascular measurements of physiological variables in a living body. The sensor guide wire (1) comprises at least two elongate sections, a first tubular elongate section (2) being tubular in the longitudinal direction of the sensor guide wire (1), and a second elongate section (3) that is adapted to be inserted a predetermined distance (5) into said first tubular section (2), a sensor element (10) provided in the distal part of said sensor guide wire (1), for measuring the physiological variable and to generate a sensor signal in response to said variable, at least one signal transmitting cable connected to the sensor element (10) to transmit sensor signals to a male connector provided in the proximal part of said sensor guide wire (1). The tubular section (2) is provided with at least one through-going opening (4) in a direction perpendicular to the longitudinal direction of the guide wire (1) and positioned a second predetermined distance (6) from one end of the tubular section (2), wherein the guide wire (1) comprises a locking member (7) to be fitted into the opening (4) in order to join the sections (2, 3) together when the second elongate section (3) is inserted into the tubular section (2).

14 Claims, 2 Drawing Sheets

Section F-F

JOINING OF SENSOR GUIDE WIRE

FIELD OF THE INVENTION

The present invention relates to a sensor guide wire, for intravascular measurements of physiological variables in a living body, comprising a first tubular section and a second elongate section, according to the preamble of the independent claims.

The present inventions also relates to a method for joining a first tubular elongated section with a second elongate section of a sensor guide wire.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient. For most applications it is also required that the sensor is electrically energized.

Some means of signal and energy transmission is thus required, and most commonly extremely thin electrical cables are provided inside a guide wire, which itself is provided in the form of a tube which often has an outer diameter in the order of 0.35 mm, and oftentimes is made of steel. In order to increase the bending strength of the tubular guide wire, a core wire is generally positioned inside the tube. The mentioned electrical cables are then positioned in the space between the inner lumen wall and the core wire.

A sensor guide wire assembly in accordance with a conventional design generally comprises different sections, such as a male connector, a shaft region, a flexible region, a sensor region and a tip region.

As is generally known in the art, the mechanical properties (e.g. flexibility and strength) of the sensor guide wire will mainly be determined by the design and dimensions of the core wire, and the materials used in the different sections of the guide wire.

It has been proved to be advantageous to use stainless steel or a super elastic alloy, such as Nitinol (NiTi), in the manufacturing of the different parts of the guide wire.

For example, EP1475036 A1, discloses a guide wire wherein the core wire is made from stainless steel or Nitinol.

However, a problem arises when it is desirous to join sections of a guide wire made from different materials, for example one section from stainless steel and another section of the guide wire made from Nitinol (NiTi), due to the fact these two materials are non weld-compatible metals. The difficulty of joining the different materials by welding results in that the joints between the different parts or regions of the guide wire becomes unreliable. Thus, the joined sections will not be securely fastened to each other.

The object of the present invention is therefore to provide a secure way of joining sections of a guide wire made from different non weld-compatible metals The object is also to facilitate the assembly of the different parts of the sensor guide wire.

SUMMARY OF THE INVENTION

The above-mentioned object is achieved by the present invention according to the independent claim.

Preferred embodiments are set forth in the dependent claims.

Thus, the present invention relates to a sensor guide wire for intravascular measurements of physiological variables in a living body, comprising at least two elongate sections, a first tubular elongate section being tubular in the longitudinal direction of the sensor guide wire, and a second elongate section that is adapted to be inserted a predetermined distance into said first tubular section, a sensor element provided in the distal part of said sensor guide wire, for measuring the physiological variable and to generate a sensor signal in response to said variable, at least one signal transmitting cable connected to the sensor element to transmit sensor signals to a male connector provided in the proximal part of said sensor guide wire. The tubular section is provided with at least one through-going opening in a direction perpendicular to the longitudinal direction of the guide wire and positioned a second predetermined distance from one end of the tubular section, wherein the guide wire comprises a locking member to be fitted into the opening in order to join the sections together when the second elongate section is inserted into the tubular section.

SHORT DESCRIPTION OF THE APPENDED DRAWINGS

DETAILED DESCRIPTION OF PREFERRED EMBODIMENTS OF THE INVENTION

Figure 1:
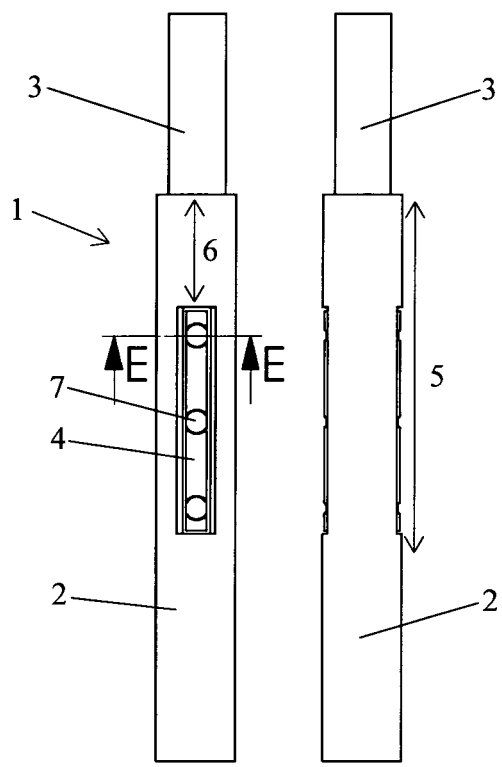
FIG. 1 shows two side views of a first and a second section of a guide wire joined together according to the present invention.

With reference to FIG. 1, a part of a sensor guide wire 1 for intravascular measurements of physiological variables in a living body, is illustrated. The guide wire 1 comprises at least two elongate sections, a first tubular elongate section 2 being tubular in the longitudinal direction of the sensor guide wire 1, and a second elongate section 3 that is adapted to be inserted a predetermined distance 5 into said first tubular section 2. A sensor element (10) (shown in FIG. 3) is provided in the distal part of said sensor guide wire 1, for measuring the physiological variable and to generate a sensor signal in response to said variable. At least one signal transmitting cable (not shown) is connected to the sensor element to transmit sensor signals to a male connector (not shown) provided in the proximal part of said sensor guide wire 1.

The tubular section 2 is provided with at least one through-going opening 4 in a direction perpendicular to the longitudinal direction of the guide wire 1 and positioned a second predetermined distance 6 from one end of the tubular section 2, wherein the guide wire 1 comprises a locking member 7 to be fitted into the opening 4 in order to join the sections 2, 3 together when the second elongate section 3 is inserted into the tubular section 2.

The predetermined distance 5 is 1 to 80 mm and the predetermined distance 6 is between 0.1 and 50 mm, preferably 1 mm.

In a preferred embodiment according to the present invention, as illustrated in FIG. 1, the through-going opening 4 of the first section 2 is in the form of an elongate slot in the longitudinal direction of the guide wire 1. A plurality of locking members 7 may then be arranged in the elongate through-going opening 4. According to the embodiment shown in FIG. 1, the three locking members 7 are arranged at equal distances from each other in the elongate through-going opening 4.

The preferred embodiment according to FIG. 1 is advantageous since the mounting of the locking members 7 is facilitated with a through-going opening in the form of an elongate slot. However, the through-going opening 4 can also be in the form of a circular through-going opening 4 or a plurality of circular through-going openings 4 arranged next to each other in the longitudinal direction, or distributed around the first section 2. The through-going opening 4 may also be distributed in any other suitable way on the first section 2, and may also have any other suitable form.

Figure 2:
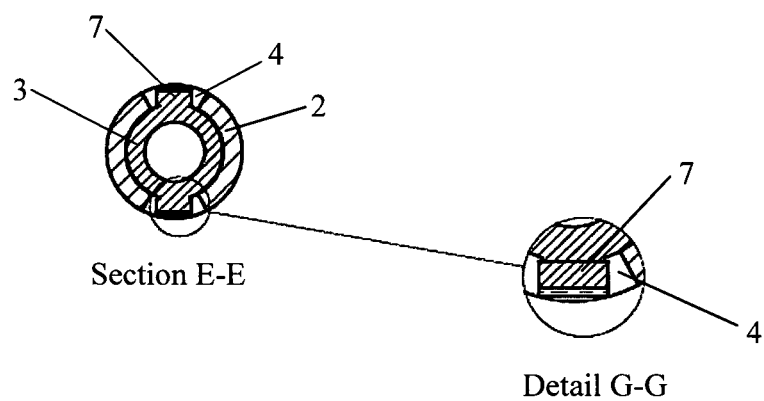
FIG. 2 shows a cross-section E-E and a detail G-G of the guide wire in FIG. 1.

According to the embodiment shown in FIG. 1, the tubular section 2 is provided with two opposite through-going openings 4. The locking members 7 are positioned in each of the through-going openings 4 and welded onto the second section 3, in order to join the locking members 7 to the second section 3, as illustrated in FIG. 2. As an alternative to welding, other suitable techniques for fastening the locking member 7 onto the second section 3 can be used, such as soldering, gluing, or similar. The locking member 7 is preferably made from the same material as the second section 3 is made from. As an alternative the locking member 7 is made from a material that easily may be welded onto section 3.

In another preferred embodiment of the present invention an elongate locking member 7 (not shown) is arranged in the through-going opening 4 of the first section 2, the elongate locking member 7 is then joined to the second section 3 by multiple bonding joints.

Figure 3:
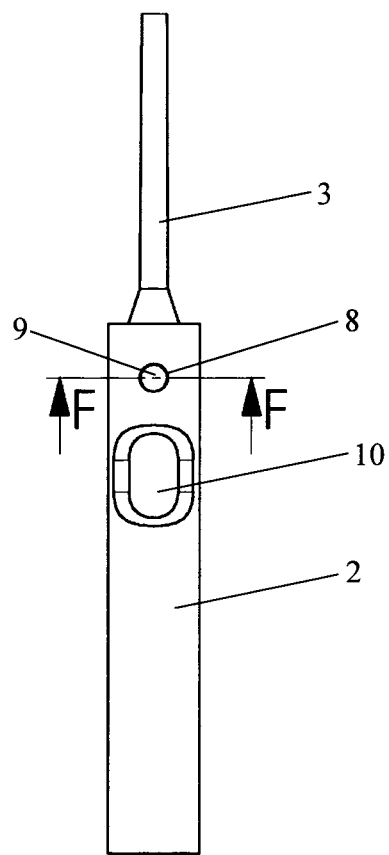
FIG. 3 shows a side view of a first and a second section of a guide wire joined together by means of a locking pin according to the present invention.
Figure 4:
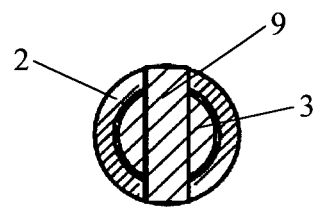
FIG. 4 shows a cross-section F-F of the guide wire in FIG. 3.

According to another preferred embodiment, as illustrated in FIGS. 3 and 4, the second elongate section 3 is provided with a through-going hole 8 in a direction perpendicular to the longitudinal direction of the guide wire 1 to coincide with the through-going opening 4 of the first section 2, wherein the locking member 7, being in the form of a locking pin 9, is adapted to be inserted through the opening 4 and the through-going hole 8 to join the first section 2 to the second section 3.

According to a preferred embodiment of the present invention one of the first 2 or the second section 3 is made from stainless steel and the other is made from a super elastic alloy. The super elastic alloy may be, nitinol (NiTi), copper-tin, copper-zinc, or copper-zinc-tin.

The first and second sections 2, 3 are, according to the present invention, different parts of the sensor guide wire 1 such as a core wire, a sensor jacket, a male connector, a shaft region, a sensor region, or a tip region. However, the first and the second section 2, 3 can also be portions of a male connector, a shaft region, a sensor region, or a tip region.

The method used for joining the first tubular elongate section 2 with the second elongate section 3 of a sensor guide wire 1, as shown in FIGS. 1 and 2, includes the steps of:
 a) inserting a second elongate section 3 a predetermined distance 5 into a first tubular section 2 of a sensor guide wire 1
 b) inserting the locking element 7 into the through-going opening 4.

The method according to one preferred embodiment of the present invention further includes the step of:
 c) welding the locking member(s) 7 onto the second elongate section 3.

In the embodiment illustrated in FIGS. 3 and 4, step a) according to the method further includes the sub step of:
 a1) aligning the through-going opening 4 in the first tubular section 2 to the through-going hole 8 in the second elongate section 3,
and further, after step b), including the steps of:
 b1) inserting the locking member 7, being in the form of a locking pin 9, further into the through-going hole 8 in the second elongate section 3
 b2) securing the locking pin 9.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for intravascular measurement of a physiological variable in a living body, comprising:
 at least two elongate sections, a first tubular elongate section being tubular in a longitudinal direction of the sensor guide wire, and a second elongate section that is adapted to be inserted a first predetermined distance into said first tubular elongate section,
 a sensor element provided in a distal part of said sensor guide wire, for measuring the physiological variable and to generate a sensor signal in response to said variable, and
 at least one signal transmitting signal line connected to the sensor element to transmit the sensor signal to a connector provided in a proximal part of said sensor guide wire,
 wherein the first tubular elongate section is provided with at least one through-going opening in a direction perpendicular to the longitudinal direction of the guide wire and positioned a second predetermined distance from one end of the first tubular elongate section, and
 wherein the guide wire comprises a locking member that is configured to be inserted into the through-going opening from outside the first tubular elongate section and attached to an outer surface of the second elongate section.

2. The sensor guide wire according to claim 1, wherein the first tubular elongate section is provided with two opposite through-going openings.

3. The sensor guide wire according to claim 2, wherein one locking member is positioned in each of the through-going openings and welded onto the second elongate section.

4. The sensor guide wire according to claim 1, wherein the locking member is made from the same material as the second elongate section.

5. The sensor guide wire according to claim 1, wherein the through-going opening of the first tubular elongate section is in a form of an elongate slot in the longitudinal direction of the guide wire.

6. The sensor guide wire according to claim 5, wherein a plurality of locking members are arranged in the elongate slot.

7. The sensor guide wire according to claim 1, wherein one of the first tubular elongate and second elongate sections is made from stainless steel and the other of the first tubular elongate and second elongate sections is made from a super elastic alloy.

8. The sensor guide wire according to claim 7, wherein the super elastic alloy is nitinol (NiTi).

9. The sensor guide wire according to claim 1, wherein said first tubular elongate and second elongate sections are different parts of the sensor guide wire selected from the group consisting of a core wire, a sensor jacket, a male connector, a shaft region, a sensor region, or a tip region.

10. The sensor guide wire according to claim 1, wherein said first tubular elongate and second elongate sections are portions of a male connector, a shaft region, a sensor region, or a tip region.

11. The sensor guide wire according to claim 1, wherein the first tubular elongate section and the second elongate section are securely fastened to each other.

12. A method for joining a first tubular elongate section with a second elongate section of a sensor guide wire for intravascular measurement of a physiological variable in a living body comprising: at least two elongate sections, the first tubular elongate section, which is tubular in a longitudinal direction of the sensor guide wire, and the second elongate section, which is adapted to be inserted a first predetermined distance into said first tubular elongate section, a sensor element provided in a distal part of said sensor guide wire, for measuring the physiological variable and to generate a sensor signal in response to said variable, and at least one signal transmitting signal line connected to the sensor element to transmit the sensor signal to a connector provided in a proximal part of said sensor guide wire, wherein the first tubular elongate section is provided with at least one through-going opening in a direction perpendicular to the longitudinal direction of the guide wire and positioned a second predetermined distance from one end of the first tubular elongate section, and wherein the guide wire comprises a locking member that is configured to be inserted into the through-going opening from outside the first tubular elongate section and attached to an outer surface of the second elongate section, the method including the steps of:

a) inserting the second elongate section the first predetermined distance into the first tubular elongate section of the sensor guide wire, and
 b) inserting the locking member into the through-going opening.

13. The method according to claim 12, further including the step of:
 c) welding the locking member onto the second elongate section.

14. A sensor guide wire for intravascular measurement of a physiological variable in a living body, comprising:
 at least two elongate sections, a first tubular elongate section being tubular in a longitudinal direction of the sensor guide wire, and a second elongate section that is adapted to be inserted a first predetermined distance into said first tubular elongate section,
 a sensor element provided in a distal part of said sensor guide wire, for measuring the physiological variable and to generate a sensor signal in response to said variable, and
 at least one signal transmitting signal line connected to the sensor element to transmit the sensor signal to a connector provided in a proximal part of said sensor guide wire,
 wherein the first tubular elongate section includes at least two through-going openings in a direction perpendicular to the longitudinal direction of the guide wire and positioned a second predetermined distance from one end of the first tubular elongate section,
 wherein the second elongate section includes at least one through-going hole in the direction perpendicular to the longitudinal direction of the guide wire to coincide with the through-going openings of the first tubular elongate section, and
 wherein the sensor guide wire comprises a locking pin configured to be inserted through the at least two through-going openings and the at least one through-going hole so as to join the first tubular elongate section to the second elongate section.

\* \* \* \* \*